United States Patent
Bulan et al.

(10) Patent No.: US 12,291,595 B2
(45) Date of Patent: May 6, 2025

(54) METHOD FOR ISOCYANATE AND POLYURETHANE PRODUCTION WITH IMPROVED SUSTAINABILITY

(71) Applicant: COVESTRO INTELLECTUAL PROPERTY GMBH & CO. KG, Leverkusen (DE)

(72) Inventors: Andreas Bulan, Langenfeld (DE); Rainer Weber, Odenthal (DE)

(73) Assignee: COVESTRO INTELLECTUAL PROPERTY GMBH & CO. KG, Leverkusen (DE)

( * ) Notice: Subject to any disclaimer, the term of this patent is extended or adjusted under 35 U.S.C. 154(b) by 358 days.

(21) Appl. No.: 17/774,163

(22) PCT Filed: Nov. 5, 2020

(86) PCT No.: PCT/EP2020/081202
§ 371 (c)(1),
(2) Date: May 4, 2022

(87) PCT Pub. No.: WO2021/089737
PCT Pub. Date: May 14, 2021

(65) Prior Publication Data
US 2022/0389150 A1    Dec. 8, 2022

(30) Foreign Application Priority Data
Nov. 6, 2019 (EP) .................................... 19207406

(51) Int. Cl.
*C07C 263/10* (2006.01)
*C01B 32/80* (2017.01)
(Continued)

(52) U.S. Cl.
CPC .............. *C08G 18/48* (2013.01); *C01B 32/80* (2017.08); *C07C 263/10* (2013.01); *C08J 11/12* (2013.01);
(Continued)

(58) Field of Classification Search
CPC .................................................... C07C 263/10
See application file for complete search history.

(56) References Cited

U.S. PATENT DOCUMENTS

| 6,022,634 | A | 2/2000 | Ramunni et al. |
| 2007/0286793 | A1* | 12/2007 | Weber .................. C01B 7/04 423/500 |

(Continued)

FOREIGN PATENT DOCUMENTS

| DE | 102005032663 A1 | 1/2007 |
| EP | 1103636 A1 | 5/2001 |

(Continued)

OTHER PUBLICATIONS

International Search Report and Written Opinion received for PCT Patent Application No. PCT/EP2020/081202, mailed on Jan. 19, 2021, 13 pages. (3 pages of English Translation and 10 pages of Original Document).

*Primary Examiner* — Michael L Leonard
(74) *Attorney, Agent, or Firm* — K&L Gates LLP

(57) ABSTRACT

The invention relates to a method for producing isocyanates and optionally polyurethanes by at least: synthesising (1) phosgene (20) from carbon monoxide (21) and chlorine (22); reacting (2) phosgene (20) with diamines (23) to form diisocyanates (24) and hydrogen chloride (25); providing a carbon dioxide gas flow (31); and cleaning (4) the carbon dioxide gas flow (31) of additional components, wherein the carbon dioxide is converted by means of an RWGS reaction (6) to form carbon monoxide (21) and hydrogen (29), which are used as raw materials for the polyurethane production, as (Continued)

Figure 1:
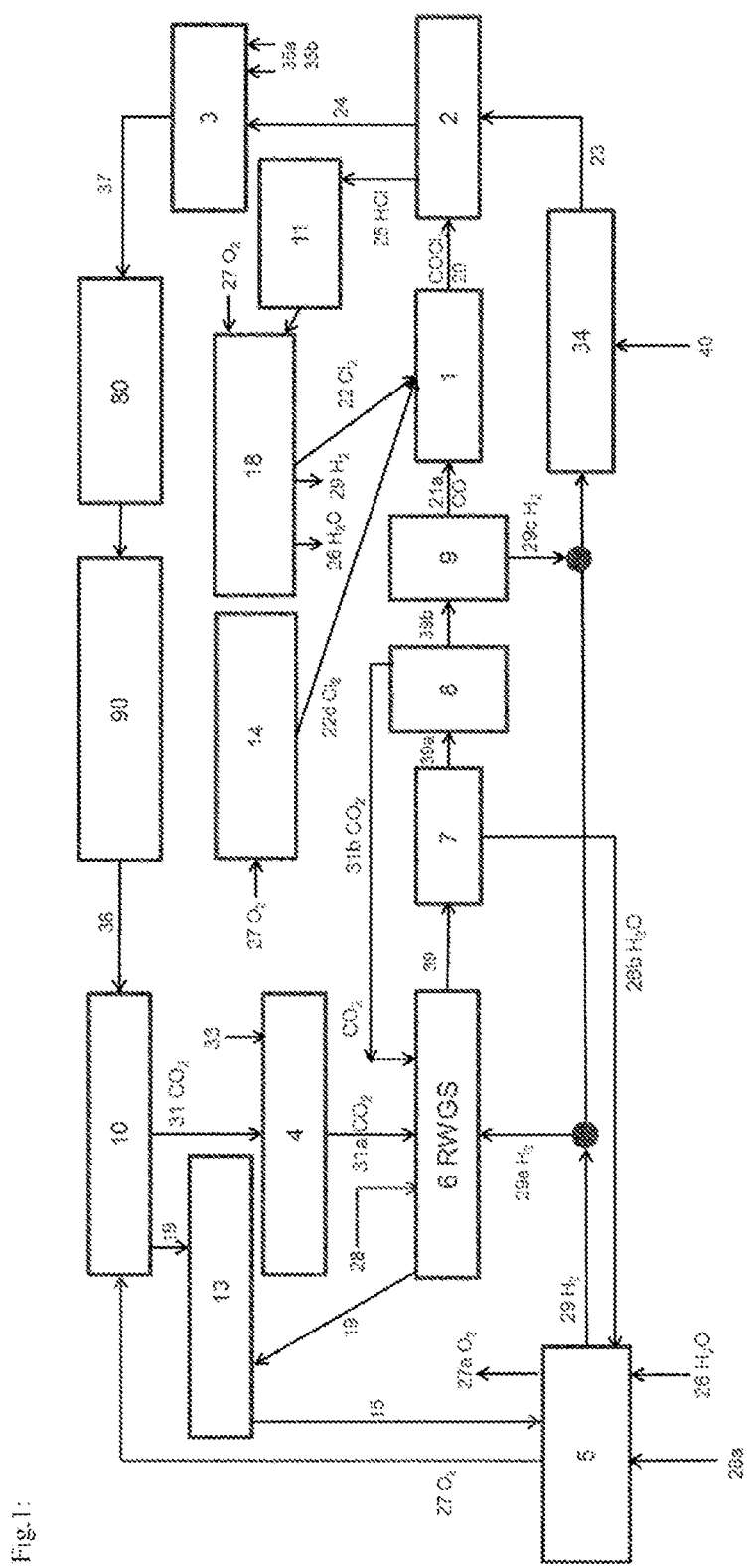

well as optionally reacting (3) the diisocyanates (24) with polyether polyol (35a) and/or polyester polyol (35b) to form polyurethanes (37).

12 Claims, 2 Drawing Sheets

(51) Int. Cl.
    *C08G 18/48*     (2006.01)
    *C08J 11/12*     (2006.01)
    *C25B 1/04*     (2021.01)
    *C25B 1/26*     (2006.01)
    *C25B 15/08*     (2006.01)

(52) U.S. Cl.
    CPC .................. *C25B 1/04* (2013.01); *C25B 1/26* (2013.01); *C25B 15/081* (2021.01); *C08J 2375/04* (2013.01)

(56) References Cited

U.S. PATENT DOCUMENTS

| | | | |
|---|---|---|---|
| 2008/0267846 A1* | 10/2008 | Haas | C01B 7/0706 423/243.1 |
| 2010/0041915 A1* | 2/2010 | Woelfert | C07C 263/10 560/347 |
| 2011/0224395 A1 | 9/2011 | Carr et al. | |
| 2014/0194641 A1 | 7/2014 | Teamey et al. | |
| 2015/0336795 A1 | 11/2015 | Kern et al. | |

FOREIGN PATENT DOCUMENTS

| | | |
|---|---|---|
| WO | 03/31690 A2 | 4/2003 |
| WO | 2009/007366 A2 | 1/2009 |
| WO | 2012/025483 A2 | 3/2012 |

\* cited by examiner

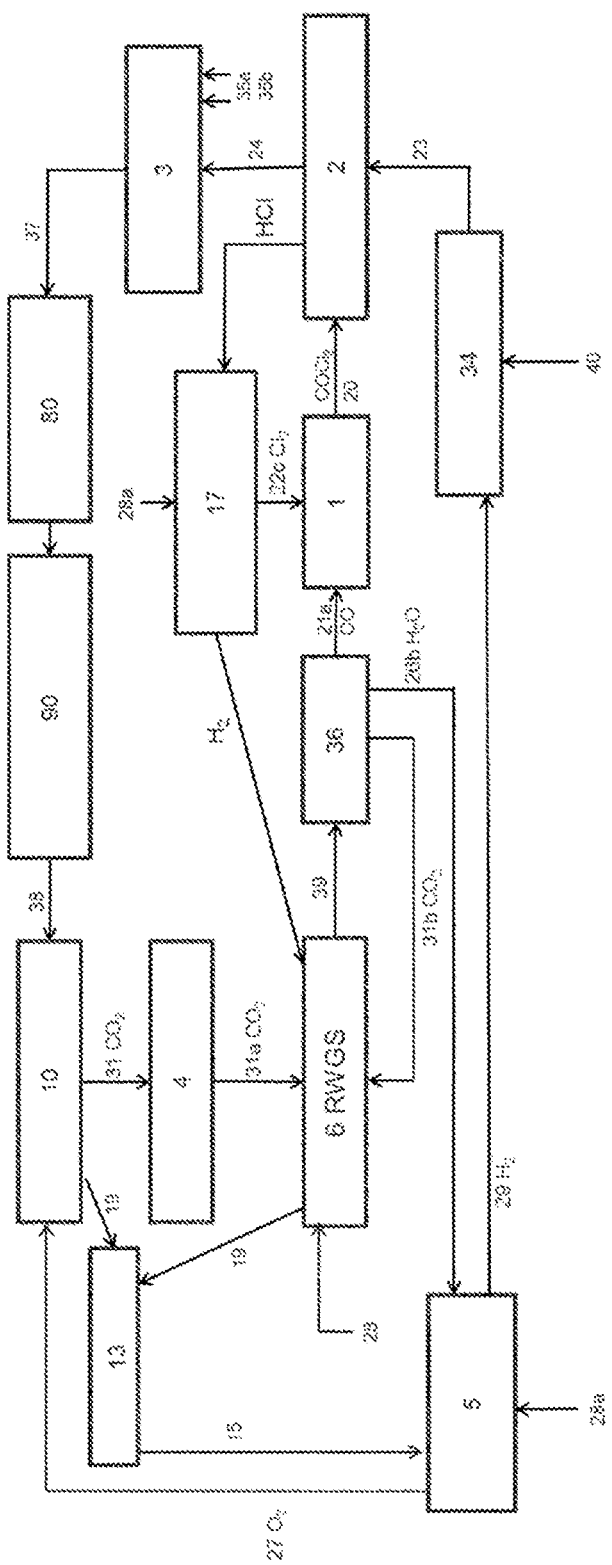

METHOD FOR ISOCYANATE AND POLYURETHANE PRODUCTION WITH IMPROVED SUSTAINABILITY

CROSS-REFERENCE TO RELATED APPLICATIONS

This application is a national stage application (under 35 U.S.C. § 371) of PCT/EP2020/081202, filed Nov. 5, 2020, which claims benefit of European Application No. 19207406.0, filed Nov. 6, 2019, both of which are incorporated herein by reference in their entirety.

The invention relates to a process for producing isocyanates and optionally polyurethanes by synthesizing phosgene from carbon monoxide and chlorine, reacting phosgene with diamines to form diisocyanates and hydrogen chloride, optionally reacting the diisocyanates with polyethers and/or polyesters to form polyurethanes, providing a carbon dioxide gas stream and purifying the carbon dioxide gas stream of secondary constituents, and subsequently reacting the carbon dioxide to produce carbon monoxide, which is used in the phosgene synthesis.

The invention further relates to the utilization of polyurethane-containing waste materials (hereinafter also referred to as "polyurethane material waste") to produce chemical feedstocks for the production of isocyanates and optionally then polyurethanes, in which polyurethane material waste is used to generate carbon dioxide and hydrocarbons and possibly carbon monoxide and hydrogen, for example by pyrolysis, the carbon dioxide is reacted with hydrogen to form carbon monoxide in a so-called reverse water-gas shift reaction (hereinafter referred to as RWGS reaction), and the carbon monoxide obtained is converted into isocyanate via phosgene and the isocyanate can be processed further into new polyurethane material.

The invention relates in particular to a process for the low-emission production of isocyanates using an RWGS reaction and to the provision of hydrogen from a water electrolysis or from an electrolysis for the production of chlorine, and also to the use of oxygen from the water electrolysis for burning materials containing polyurethane to carbon dioxide and optionally burning pyrolysis residues obtained from materials containing polyurethane and use of the carbon dioxide obtained in each case as a feedstock for the RWGS reaction.

The carbon monoxide, preferably produced from utilization of polyurethane material waste, is reacted with chlorine to form phosgene and this is reacted with amines to form isocyanates. The isocyanates can, through reaction with a polyether polyol or polyester polyol, be used to produce fresh polyurethane materials. This closes a section of the value chain. If $CO_2$ and electricity from renewable energy sources are used for the water electrolysis, it is possible to produce polyurethane material with a further improvement in sustainability. The proportion of fossil carbon in the polyurethane should be significantly reduced.

Furthermore, through the water electrolysis it is possible to produce hydrogen additionally required for the hydrogenation of nitro compounds to amines, which can be converted into isocyanates with phosgene. In the water electrolysis, oxygen is generated at the anode as a coproduct. This oxygen can be used for burning the polyurethane-containing waste materials and the pyrolysis residue, giving rise during burning to a highly concentrated $CO_2$ offgas stream and making $CO_2$ recovery significantly more economical than when the waste containing polyurethane material is burned with air. It is however also possible to use $CO_2$ from alternative sources such as the burning of other wastes. The $CO_2$ is purified and supplied to the RWGS reaction.

Polyurethanes, also referred to hereinbelow as PUs for short, are plastics that result from the polyaddition reaction of polyols containing at least two hydroxyl groups with polyisocyanates. The use of diols and diisocyanates results in linear polyurethanes. Crosslinked polyurethanes can be produced by reacting triisocyanate-diisocyanate mixtures with triol-diol mixtures. The properties of PUs can be varied within a wide range. Depending on the degree of crosslinking and/or the isocyanate or OH component used, thermosets, thermoplastics or elastomers are obtained. Polyurethanes are however also used as molding compounds for compression molding, as casting resins (isocyanate resins), as (textile) elastic fibers, polyurethane coatings, and as polyurethane adhesives. It is also very easy to produce foams from polyurethane.

Flexible PU foams are used for a great many purposes, especially as upholstery material, for example for furniture and car seats, as mattress foam, as carpet backing material, for textile lamination, as cleaning sponge or as filter material.

Rigid PU foams are used mainly for thermal insulation, for example in buildings, cooling devices, hot and cold storage, and for some pipe systems (plastic jacket composite pipes, flexible composite pipes).

There are other, relatively new areas of application for PU foams in vehicle construction, such as steering wheels, armrests, soft coating of handles, interior trim, dashboards, sound insulation, rattle protection, seals, transparent coating of wood decors.

At the end of the use phase of products containing PU materials, they are usually disposed of, i.e. stored in landfills or incinerated in waste incineration plants. Thus far, it has not yet been possible to make use of the materials in an economically successful manner, i.e. it has thus far not been possible to recover the employed polyols or polyisocyanates from the PU materials in an economical yield.

One approach to material recycling of PUs is glycolysis, in which the urethane group is reacted with glycol to form carbamate and a polyol.

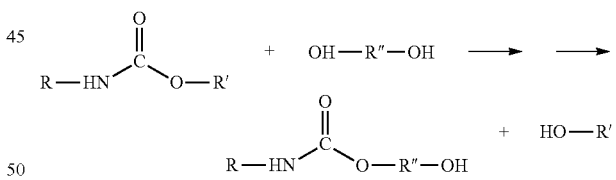

The urethane group can also be reacted with an amine to form urea and a polyol.

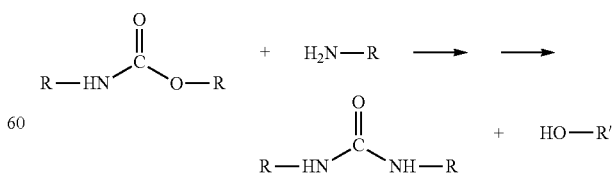

The object of the present invention was to find a more sustainable process for isocyanate production and ultimately also for polyurethane production, including recycling processes and closing of value chains. Up to now, essential components for polyurethane production such as carbon monoxide, hydrogen or the electricity for electrolysis operations such as water electrolysis and chloralkali electrolysis have been produced from fossil fuels. For example, carbon monoxide and hydrogen are conventionally obtained from natural gas or coal by means of reforming processes, and chlorine is obtained from electrolysis with electricity produced using fossil fuels such as oil, coal or natural gas.

The "sustainability" of a process is understood by those skilled in the art according to the definition of sustainability (sustainable development) coined by the UN in the Brundtland Report of the "World Commission on Environment and Development", this being that the execution of the process in the present makes the smallest possible contribution, or none at all, to compromising the ability of future generations to meet their own needs, in particular needs in respect of the use of resources such as fossil raw materials and especially in respect of the conservation of living space, for example the protection of the earth's atmosphere. It is thus an object of the invention to make the production of isocyanate and optionally polyurethane more sustainable than the production methods known from the prior art. The contribution of the production of isocyanate, and thus of polyurethane, to a decreasing ability to meet the needs of fixture generations should be reduced or even avoided.

An object of the invention is thus to reduce the use of fossil feedstocks as a reactant for isocyanate production and possibly also the use of fossil feedstocks to provide energy for isocyanate production. The latter object in particular should further improve the carbon footprint of PU production in order to protect the earth's atmosphere.

The invention relates to a process for producing isocyanates (and optionally polyurethanes) by at least the following steps:
   synthesizing phosgene from carbon monoxide and chlorine,
   reacting phosgene with diamines to form diisocyanates and hydrogen chloride,
   providing a $CO_2$ gas stream,
   purifying the $CO_2$ gas stream of secondary constituents, in particular of nitrogen oxides, sulfur compounds, dust, water, oxygen and HCl, optionally by means of adsorption, gas scrubbing or catalytic treatment to obtain a purified carbon dioxide,
   electrolyzing water to hydrogen and oxygen,
   providing the hydrogen stream and feeding together with the purified $CO_2$ gas stream into an RWGS reaction zone and reacting the reactants according to the principle of the RWGS reaction to form a product gas mixture consisting of water vapor, CO, and any by-products, in particular lower hydrocarbons, particularly preferably methane,
   separating off the water of the water vapor from the product gas mixture and recycling the water to the water electrolysis,
   separating off unreacted carbon dioxide from the gas mixture of the RWGS reaction obtained from the separation, in particular by means of amine scrubbing, and recycling the unreacted carbon dioxide to the RWGS reaction,
   separating off the hydrogen that has not reacted in the RWGS reaction from the gas mixture of carbon monoxide and hydrogen obtained after the separation, in particular using a cold box, and optionally recycling the hydrogen to the RWGS reaction or feeding the hydrogen into the hydrogenation of dinitro compounds for the production of diamines as feedstock for the diisocyanate,
   feeding the remaining carbon monoxide from the separation into the phosgene synthesis,
   feeding the hydrogen from the water electrolysis, optionally together with unreacted hydrogen from the RWGS reaction, into the hydrogenation of nitro compounds for the production of diamines,
   separating off and purifying the hydrogen chloride formed in isocyanate production and subsequent oxidative reaction of the hydrogen chloride in the form of a reaction in a thermocatalytic gas-phase oxidation with oxygen to chlorine and water and/or in the form of an electrochemical oxidation of the hydrogen chloride to chlorine and/or in the form of an electrochemical oxidation of the hydrogen chloride to chlorine and hydrogen by HCl diaphragm electrolysis,
   supplying the previously formed chlorine to the phosgene synthesis, optionally alongside feeding in fresh chlorine from a chloralkali electrolysis.

For the production of polyurethanes, a step for reacting the diisocyanates with polyether polyol and/or polyester polyol to form polyurethanes can additionally be included in the process of the invention.

Suitable in turn is an embodiment of the process in the form of a process for producing isocyanates and polyurethanes through
   synthesizing (1) phosgene (20) from carbon monoxide (21a) and chlorine (22),
   reacting (2) phosgene (20) with diamines (23) to form diisocyanates (24) and hydrogen chloride (25),
   reacting (3) the diisocyanates (24) with polyether polyol (35a) and/or polyester polyol (35b) to form polyurethanes (37),
   providing a $CO_2$ gas stream (31),
   purifying (4) the $CO_2$ gas stream (31) of secondary constituents, in particular of nitrogen oxides, sulfur compounds, dust, water, oxygen and HCl optionally by means of adsorption, gas scrubbing or catalytic treatment to obtain a purified carbon dioxide (31a),
   electrolyzing (5) water (26) to hydrogen (29) and oxygen (27),
   providing the hydrogen stream (29a) and feeding together with the purified $CO_2$ gas stream (31a) into an RWGS reaction zone and reacting (6) the reactants according to the principle of the RWGS to form a product gas mixture (39) consisting of water vapor (26b), CO (21), and any by-products (32), in particular lower hydrocarbons, particularly preferably methane,
   separating off (7) the water of the water vapor (26b) from the product gas mixture (39) and recycling the water to the water electrolysis (5),
   separating off (8) unreacted carbon dioxide (31b) from the gas mixture (39a) of the RWGS reaction (6) obtained from the separation (7), in particular by means of amine scrubbing, and recycling the unreacted carbon dioxide (31b) to the RWGS reaction (6),
   separating off (9) the hydrogen (29a) that has not reacted in the RWGS reaction (6) from the gas mixture (39b) of carbon monoxide (21a) and hydrogen (29c) obtained after the separation (8), in particular using a cold box, and optionally recycling the hydrogen (29c) to the RWGS reaction (6) or feeding the hydrogen (29c) into the hydrogenation (34) of dinitro compounds for the production of diamines (23) as feedstock for the diisocyanate (24), feeding the remaining carbon monoxide (21a) from the separation (9) into the phosgene synthesis (1), feeding the hydrogen (29) from the water electrolysis (5), optionally together with unreacted hydrogen (29c) from the RWGS reaction (6), into the hydrogenation of nitro compounds (34) for the production (2) of diamines (23), separating off and purifying (11) the hydrogen chloride (25) formed in isocyanate production (2) and subsequent oxidative reaction (18) of the hydrogen chloride (25) in the form of a reaction in a thermocatalytic gas-phase oxidation (16) with oxygen (27) to chlorine (22a) and water (26) and/or in the form of an electrochemical oxidation (12) of the hydrogen chloride (25) to chlorine (22b) and/or in the form of an electrochemical oxidation (17) of the hydrogen chloride (25) to chlorine (22c) and hydrogen (29) by HCl diaphragm electrolysis (17), supplying the previously formed chlorine (22a, 22b, 22c) to the phosgene synthesis (1), optionally alongside feeding in fresh chlorine (22d) from a chloralkali electrolysis (14).

All the embodiments and definitions hereinbelow apply equally to the abovementioned variants of the process of the invention:

"Lower hydrocarbons" are in accordance with the invention understood as meaning hydrocarbons having 1 to 8 carbon atoms.

"Amine scrubbing" of the product gas of the RWGS reaction is here understood as meaning in particular the generally known scrubbing of the gas mixture according to the principle of chemisorption with amines such as monoethanolamine (MEA), diethanolamine (DEA), methyldiethanolamine (MDEA) or diglycolamine (DGA), which even at relatively low pressure in an absorption column achieves a high purity of the purified gas mixture.

"Renewable energy" is understood by those skilled in the art as meaning energy from an energy source that does not become exhausted, such as wind energy, hydro energy or solar energy.

A preferred embodiment of the process of the invention is characterized in that carbon dioxide formed from the utilization of polyurethane material waste by burning and/or by pyrolysis is used for the RWGS synthesis. In this case, it is in turn preferable when oxygen gas obtained from the water electrolysis is used for burning.

The "polyurethane material waste" may have arisen through the use of commercial polyurethane, the polyurethane having been produced from diisocyanates provided by the process of the invention. When reutilizing a polyurethane material waste of this nature in the RWGS synthesis of the invention, the process is said to be a "closed loop" process. However, it is of course also possible in the RWGS synthesis of the present invention to utilize polyurethane material waste originating from polyurethanes that had not been produced from diisocyanates from the process of the invention.

Very particular preference is given to a process in which carbon dioxide used for the RWGS synthesis is formed from utilizing polyurethane material waste by burning in the presence of gas having a content of oxygen gas ($O_2$), said gas having a content of oxygen gas ($O_2$) of at least 30% by volume, preferably at least 50% by volume, particularly preferably of at least 95% by volume, very particularly preferably of at least 99% by volume, most preferably of at least 99.5% by volume.

The oxygen gas used for burning can in turn preferably be obtained from the water electrolysis.

The polyurethane material waste is utilized for example by pyrolyzing said polyurethane material waste at elevated temperature, optionally in the presence of a catalyst, to obtain carbon dioxide, possibly carbon monoxide, possibly hydrogen, possibly a mixture of aliphatic and aromatic low-molecular-weight hydrocarbons and nitrogen-containing hydrocarbons, and possibly a residue of higher-molecular-weight hydrocarbons. The mixture obtained in the pyrolysis is then preferably subjected to refining to obtain a gas mixture of carbon dioxide, carbon monoxide, hydrogen gas, and other low-molecular-weight hydrocarbon compounds that are gaseous under standard conditions.

The burning of the residue obtained in the pyrolysis and optionally of any other polyurethane material waste can be effected in particular with oxygen-containing gas, in particular with pure oxygen, to obtain gas containing carbon dioxide.

In a preferred embodiment of the novel process, the RWGS synthesis uses carbon dioxide formed from burning polyurethane material waste using oxygen obtained from water electrolysis.

In a further preferred embodiment of the novel process, the water electrolysis and/or the electrochemical oxidation is performed using electricity generated from renewable energy, in particular electricity optionally obtained through the use of wind power, solar energy or hydro power.

In another preferred embodiment of the novel process, the water electrolysis and/or the electrochemical oxidation are performed using electricity from feedback energy obtained from burning used polyurethane material and/or from performing the RWGS reaction.

A further alternative embodiment of the novel process is characterized in that the RWGS reaction is performed using electricity generated from renewable energy, in particular electricity optionally obtained through the use of wind power, solar energy or hydro power.

In a further alternative embodiment of the novel process, the RWGS reaction is heated by means of feedback energy obtained from burning polyurethane material waste. "Feedback energy" is understood by those skilled in the art as meaning energy, especially thermal energy, that is taken from a process step of the process of the invention (optionally converted into another form of energy, for example electricity) and reintroduced into another process step of the process of the invention.

In a preferred variant of the novel process, the RWGS reaction is heated by burning hydrocarbons from renewable hydrocarbon production, in particular by burning biomethane. Biomethane is here understood as meaning methane obtained from the biogas that is produced by the fermentation of biomass. A further particularly preferred variant of the novel process is characterized in that the polyurethane material is, after having been used, recycled as polyurethane material waste and that the polyurethane material waste is burned to form carbon dioxide and the carbon dioxide used as feed material in the purification step.

The oxygen for burning is preferably obtained from a water electrolysis.

By preferably using electricity from renewable energy (preferably from wind power, hydro power or from solar energy), $CO_2$ emissions in the process overall are further reduced. In a preferred novel process, the hydrogen formed in the water electrolysis is optionally used in the optional refining step and/or in a hydrogenation of nitro compounds, wherein the amines obtained in the hydrogenation of nitro compounds can be used in isocyanate production. Any hydrogen withdrawn that is obtained in the new process is preferably used in the hydrogenation of nitro compounds. This provides access to amines as precursors of the isocyanate.

The material cycle is in a particularly preferred embodiment of the process of the invention further closed in that the polyurethane material is, after having been used, recycled as polyurethane material waste and that the polyurethane material waste is burned to form carbon dioxide and the carbon dioxide used as feed material in the purification step.

When recycling PU material at the end of its service life, conventional separation processes are used to separate composite materials in waste. The PU material for instance undergoes an automated or manual coarse separation and is then mechanically comminuted and if necessary separated further. The PU material obtained is used as a polyurethane material waste feedstock for burning or pyrolysis.

In the case of burning, the polyurethane material waste is reacted with for example pure oxygen $O_2$ evolved at the anode as by-product of the water electrolysis. The heat of reaction evolved during burning can be used as feedback energy for the production of steam and/or electricity. In particular, the heat can be used to operate the pyrolysis and the electricity generated can be used in the electrolysis. This further improves the overall efficiency of the novel process.

The heat obtained during burning can also be used as feedback energy to heat the RWGS reaction, which further improves the overall energy efficiency of the novel process compared to the prior art.

The $CO_2$ originating from burning or pyrolysis of the polyurethane material waste is obtained in highly concentrated form and is supplied to a purification step before further use. In this step, the by-products of burning, for example sulfur compounds such as $SO_2$, nitrogen compounds such as $NO_X$, and residual organics as well as dust and other compounds formed from the components present in the PU material, are separated off.

The burning of the polyurethane material waste with pure oxygen can be carried out, for example, according to the process known as the oxyfuel process in an atmosphere of pure oxygen and $CO_2$ (recirculating flue gas). The resulting flue gas is not diluted with the nitrogen present in air and consists essentially of $CO_2$ and water vapor. The water vapor can be easily condensed, with the result that a highly concentrated $CO_2$ stream (concentration in the ideal case close to 100 percent) is formed. The $CO_2$ can then be purified and further processed, optionally also compressed and stored.

In addition, some of the energy obtained from the pyrolysis or burning of the polyurethane material can be converted into steam or electricity. As already mentioned, the electricity obtained can be used to operate the electrolysis, resulting in an even more efficient process with low consumption of electrical energy.

The purification of the $CO_2$ from combustion gases can be carried out using processes generally known from the prior art. This is described by way of example hereinbelow.

The first step here is, for example, purification of the combustion gases, the main component of which is $CO_2$. The setup for a combustion gas purification is subdivided into different stages. The particular task of purification is to provide $CO_2$ for the subsequent RWGS reaction that is free of interfering secondary constituents.

In the first stage, dust is removed from the combustion gas. This can be done with fabric filters or with an electrostatic filter. Any acidic gas present, such as hydrogen chloride formed from chlorine compounds present in the waste, can then be removed. This is done using, for example, offgas scrubbing towers. The combustion gas is thereby also cooled and freed from further dusts and any heavy metals present. In addition, sulfur dioxide gas that has formed is also removed in a scrubbing circuit and reacted for example with slaked lime to form calcium sulfate. The removal of nitrogen compounds from the combustion gases can be carried out for example on catalyst-containing zeolites or by adding urea or ammonia to convert the nitrogen oxides back to nitrogen and water. In order to prevent the formation of ammonium salts, which would clog the pores of the catalyst, the catalysts are usually operated at a temperature of above 320° C. Likewise, the $N_2$ compounds can be removed by scrubbing with nitric acid or scrubbing with catalysts.

The drying and further purification of the $CO_2$ can be effected by known conventional methods. Drying for example by treatment with concentrated sulfuric acid.

In the final purification stage, activated carbon filters are used to remove any residual organics and last metal residues still present in the combustion gas by means of activated carbon. This can be done using, for example, activated carbon in dust form that is metered into the combustion gas stream or flue gas stream and then deposited again on the fabric filter together with the accumulated contaminants. The used carbon is discharged and supplied to energy recovery (described in principle in: https://www.ava-augsburg.de/umwelt/rauchgasreinigung/).

The purification processes performed on the combustion gases provide $CO_2$ that can be used as a feedstock for the RWGS reaction.

In gas streams that have a lower concentration of $CO_2$, $CO_2$ can also optionally be separated off by amine scrubbing.

In the case of pyrolysis, the supply of additional oxygen gas to the pyrolysis reaction space is not preferred. The pyrolysis of the used polyurethane material can preferably be performed as follows:

The pyrolysis of the polyurethane material is carried out at elevated temperature, optionally in the presence of a catalyst, to obtain possibly carbon dioxide, possibly carbon monoxide, possibly hydrogen, a mixture of aliphatic and aromatic low-molecular-weight hydrocarbons and nitrogen-containing hydrocarbons, and a residue of higher-molecular-weight hydrocarbon compounds,
  optionally refining the resulting mixture of low-molecular-weight hydrocarbons to obtain a mixture of gaseous and liquid hydrocarbons and a mixture of carbon dioxide and carbon monoxide, hydrogen, and other gaseous hydrocarbon compounds, and separating the resulting mixtures in a gas separation.
  burning the residue obtained and optionally further polyurethane material waste with oxygen-containing gas, in particular with pure oxygen, to obtain gas containing carbon dioxide.

The polyurethane material waste that is recycled and comminuted as described above can be supplied to the pyrolysis step, it being possible for the pyrolysis to be carried out either with or without a catalyst.

The fractions formed during the pyrolysis are gaseous, liquid and solid, with the solid phase mostly consisting mainly of pyrolytic carbon. The liquid long-chain carbon compounds comprising aromatics such as toluene, benzene, and xylene are preferably supplied to a refining process. Here, the compounds can be separated or in refining processes optionally reacted further with hydrogen, preferably hydrogen from water electrolysis, with the result that propene and ethene (as precursors for polyols, polyethers) may also be obtained. The long-chain liquid hydrocarbon compounds can be separated off and processed further. It is also possible to reuse aromatic compounds such as benzene or aniline or—if present—isocyanates as feedstocks in appropriate syntheses.

In addition, the pyrolysis can optionally be operated in particular in such a way that larger amounts of carbon monoxide and possibly hydrogen are generated. These gases can be separated off together with the short-chain hydrocarbon compounds, for example in the refining step, or they can also be separated off separately and then supplied to a carbon monoxide-hydrogen separation and used.

The solid substances obtained during the pyrolysis consist mostly of carbon. This solid phase can be reacted with pure oxygen from the water electrolysis. This also gives rise to a highly concentrated stream of $CO_2$, which is supplied to a purification step.

Another option for producing high-purity $CO_2$ is to absorb the $CO_2$ in an alkali solution, for example aqueous potassium hydroxide solution. This results in the formation of potassium hydrogen carbonate, which can then be thermally decomposed back to $CO_2$ and potassium hydroxide. Heat generated from pyrolysis or burning can be used here.

The purified $CO_2$ is supplied to the RWGS reaction.

The gas mixture taken from the RWGS reaction is cooled. On cooling, the water of reaction separates off. The water of reaction can be returned to the water electrolysis as a feedstock. After the water separation, the gas is supplied to the $CO_2$ separation.

The $CO_2$ separation is carried out for example by means of an amine scrubbing step in which the $CO_2$ is removed and the residual gas consisting of CO and $H_2$ is supplied to a $H_2$/CO gas separation unit. The CO obtained is then supplied to the phosgene synthesis and reacted here with $Cl_2$ to form phosgene. The phosgene produced is supplied to the isocyanate production. In the isocyanate production, phosgene is reacted with an amine to form an isocyanate and hydrogen chloride.

The hydrogen obtained from the water electrolysis or from the $H_2$/CO separation can either be supplied to the hydrogenation of nitro compounds to amines and hence to the production of isocyanates.

Preference is therefore given to an embodiment of the novel process in which at least substreams of carbon monoxide and/or hydrogen from the $H_2$/CO separation are supplied to an RWGS reaction.

The isocyanate from isocyanate production is reacted with polyether polyol or with polyester polyol to form polyurethane material in a corresponding synthesis.

The novel process can also preferably be operated in such a way that part of the polyurethane material waste is supplied directly for burning instead of pyrolysis.

The hydrogen chloride (HCl) produced during isocyanate production may be supplied to a different HCl recycling unit such as an HCl diaphragm or HCl electrolysis with a gas-diffusion electrode or a catalytic gas-phase oxidation. In the case of HCl electrolysis with a gas-diffusion electrode or a gas-phase oxidation, the $O_2$ required can be obtained from the water electrolysis.

The production of chlorine gas from electrochemical oxidation according to the HCl—ODC electrolysis process (for suitable electrolysis cells, see U.S. Pat. No. 6,022,634 A, WO 03/31690 A1), the production of chlorine gas from HCl diaphragm electrolysis (see EP 1 103 636 A1), the production of chlorine gas from thermocatalytic gas-phase oxidation (see WO 2012/025483 A2), and the production of chlorine from chloralkali electrolysis (see WO 2009/007366 A2) are well known to those skilled in the art. Reference is made expressly and in full to the content of the abovementioned documents cited in connection with the production of chlorine gas.

The isocyanates and the polyether polyols and optionally also polyester polyols can then be used to produce the PU materials that are needed commercially. The polyurethanes are used in various commercial applications. At the end of their useful life, the materials are supplied to a recycling unit and the PU materials separated here. The separated material is then resupplied, as polyurethane material waste, for utilization in the form of pyrolysis and/or burning.

This eliminates the need for further fossil feedstocks for isocyanate production, allowing polyurethane material to be produced in a more sustainable manner.

The invention is elucidated in more detail hereinbelow and by way of example with reference to the figures.

In the figures:

FIG. 1 shows a schematic overview of the overall process comprising the RWGS reaction, chlorine production, PU production, use, and utilization of the polyurethane material waste therefrom to afford $CO_2$ for the RWGS reaction In FIG. 1, the following reference numbers have in each case the meaning shown on the right:

1 Phosgene synthesis
2 Isocyanate production
3 Polyurethane production
4 Purification of $CO_2$ gas
5 Water electrolysis
6 RWGS reaction (reverse water-gas shift reaction)
7 Water separation
8 $CO_2$ separation
9 $H_2$/CO separation
10 Utilization of polyurethane material waste (38) through pyrolysis (10*a*) and/or burning (10*b*)
10*a* Pyrolysis
10*b* Burning
11 HCl gas separation/purification
12 Electrochemical oxidation of HCl by HCl—ODC electrolysis
13 Power and steam generation
14 Chloralkali electrolysis for production of $Cl_2$
15 Electricity from energy/steam (13)
16 $Cl_2$ production through thermocatalytic gas-phase oxidation (Deacon) of HCl
17 $Cl_2$ production through electrochemical oxidation of hydrochloric acid by diaphragm electrolysis
18 Oxidative conversion of HCl to chlorine gas in the form of (12) and/or (16) and/or (17)
19 Heat
20 Phosgene
21 Carbon monoxide in the gas stream from the RWGS reaction
21*a* Carbon monoxide from the $H_2$/CO separation
22 Chlorine gas selected from 22*a* and/or 22*b* and/or 22*c*
22*a* Chlorine gas from thermocatalytic gas-phase oxidation (16)
22*b* Chlorine gas from electrochemical oxidation according to the HCl—ODC process (12)
22*c* Chlorine gas from HCl diaphragm electrolysis (17)
22*d* Chlorine from chloralkali electrolysis (14) (preferably with oxygen-depolarized cathode (ODC) with supply of oxygen (27))
23 Diamines
24 Diisocyanates
25 Hydrogen chloride 26 Water
26b Water
27 Oxygen
27a Oxygen
28 Bio-natural gas and/or renewable energy, optionally only for heating
28a Electricity from renewable energy
29 Hydrogen from water electrolysis
29a Hydrogen from water electrolysis for the RWGS reaction
29b Hydrogen that is unreacted in the RWGS reaction
29c Hydrogen, unreacted, from the $H_2$/CO separation
31 $CO_2$ from 10
31a Purified $CO_2$
31b Unreacted $CO_2$ from $CO_2$ separation
32 By-products from the RWGS reaction
33 $CO_2$ from renewable sources
34 Hydrogenation of nitro compounds for diamine production
35a Polyether polyol
35b Polyester polyol
37 Polyurethane material
38 Waste containing polyurethane material (polyurethane material waste) for 10
39 Product gas mixture from the RWGS reaction consisting of 21, 26b, $CO_2$, 29b, and 32
39a 39 with decreased content of 26b
39b 39a with decreased content of $CO_2$
40 Nitro compounds
80 Use of 37 and/or of polyurethane material from different commercial source
90 Polyurethane-based materials—end-of-life recycling FIG. 2 shows a schematic overview of the overall process comprising the RWGS reaction, hydrochloric acid electrolysis according to the diaphragm process (HCl-DIA) for chlorine production, including optional PU production, use of the polyurethane material, and utilization of polyurethane material waste therefrom to afford $CO_2$ for the RWGS reaction.

The assignment of the reference numbers used in FIG. 2 is as defined for FIG. 1.

FIG. 1 and FIG. 2 illustrate the closed-loop variant of the process of the invention. It is of course possible in one embodiment to use, as a polyurethane material waste (38) feed, also polyurethane material that has been produced not from recycled polyurethane material (37) in the sense of a closed-loop process, but from toluene-2,4-diisocyanate that originated directly from feedstocks from fossil sources without recycling. In this variant, steps (3), (35a), (35b), and (37) are to be deleted in FIG. 1 and FIG. 2.

EXAMPLE 1

Low-Emission Production According to the Invention of Toluene Diisocyanate (TDI), CO Production by RWGS, Heating Thereof with Bio-Natural Gas, HCl Recycling by Means of HCl Gas-Phase Oxidation (Deacon), and Provision of $H_2$ from a Water Electrolysis Into an RWGS reaction chamber (6) operated at a temperature of 802° C. was introduced 17.84 t/h of $CO_2$ and 0.81 t/h of $H_2$. The product gas mixture (39) resulting from the RWGS reaction, which consisted of CO (21), $H_2O$ (26b), unreacted $CO_2$, and also unreacted $H_2$ (29a), as well as by-products (32), mainly small amounts of methane, was withdrawn and supplied to a water separation (7), affording 7.3 t/h of water. This water (26b) is returned to the water electrolysis (5). A total of 3.24 t/h of hydrogen was taken from the water electrolysis (5), which meant that an additional 21.86 t/h of water was added. The remaining gas mixture (39a) from the RWGS was supplied to a $CO_2$ separation (8). The $CO_2$ separation was effected by amine scrubbing, wherein the separated $CO_2$ (31b) was recycled to the RWGS reaction. The energy for the $CO_2$ separation from the $CO_2$-amine complex formed was obtained from the separation of water (7) from the RWGS gases (39). The gas freed of $CO_2$ (39b) was supplied to the $H_2$/CO separation (9). For the $H_2$/CO separation, a so-called cold box was employed, in which the $H_2$/CO gas mixture was cooled and hydrogen and CO were separated. The separated hydrogen (29c) was returned to the RWGS (6). 11.35 t/h of CO from the $H_2$/CO separation (9) was supplied to a phosgene synthesis (1). Here, the CO reacted with 29.79 t/h of chlorine taken from an HCl gas-phase oxidation (16). 40.15 t/h of phosgene was taken from the phosgene synthesis (1) and reacted in an isocyanate production step (2) with 24.73 t/h of toluenediamine 23 to give 35.27 t/h of toluene diisocyanate (24). This gave rise to 29.59 t/h of HCl gas (25) which, after purification by low-temperature distillation, was supplied to an HCl gas-phase oxidation (16). In the HCl gas-phase oxidation (16), the HCl gas was reacted with oxygen (27) to form chlorine and $H_2O$ at approx. 300° C. over a ruthenium oxide-based catalyst. The oxygen (27) required was taken from the water electrolysis (5). For the closed-loop variant of the process of the invention, the toluene diisocyanate (24) obtained was reacted in a conventional manner with polyether polyols (35a) or polyester polyols (35b) to form polyurethane material (37).

After use of the polyurethane material in various commercial applications (80), it could be collected and recycled (90) in order to burn (10b) the polyurethane material waste (38) resulting therefrom. Burning was here realized with oxygen (27) from the water electrolysis (5), resulting in the formation of a highly concentrated $CO_2$ offgas stream (31). This $CO_2$ stream (31) was supplied to a $CO_2$ purification (4) in which water originating from combustion and nitrogen oxides and sulfur oxides were removed. 17.84 t/h $CO_2$ was thereafter supplied to the RWGS (6). It is of course possible in one embodiment to use, as a polyurethane material waste (38) feed, also polyurethane material that has been produced not from recycled polyurethane material (37) in the sense of a closed-loop process, but from toluene-2,4-diisocyanate that originated directly from fossil sources without recycling. In this variant, steps (3), (35a), (35b), and (37) are to be deleted in FIG. 1 and FIG. 2. The hydrogen (29) was generated in a water electrolysis with a power of 45 MW in which renewable energy was used. The water electrolysis (5) was an alkaline water electrolysis operated with a current density of 8 kA/m² and a cell voltage of 2 V per electrolysis element. Supplied to this were 45 MW and 21.86 t/h of water plus 7.3 t/h of water from $H_2O$ separation (7). 3.24 t/h of $H_2$ was taken from the water electrolysis.

The RWGS reaction was operated at 802° C., the temperature was generated by burning bio-natural gas.

Through the process of the invention, 22% of the carbon present in the TDI was replaced from a non-fossil carbon source. The use of renewable energy in the water electrolysis allowed the $CO_2$ footprint of the phosgene produced from CO and $Cl_2$ to be further reduced.

EXAMPLE 2

Low-Emission Production According to the Invention of Toluene Diisocyanate (TDI), CO Production by RWGS, Heating Thereof with Bio-Natural Gas, HCl Recycling by Means of HCl Diaphragm Electrolysis, and Provision of $H_2$ for the Hydrogenation of Dinitrotoluene from a Water Electrolysis Into an RWGS reaction chamber (6) operated at a temperature of 802° C. was introduced 17.84 t/h of $CO_2$ and 0.81 t/h of $H_2$. The hydrogen originated from HCl recycling by HCl diaphragm electrolysis. The product gas mixture (39) resulting from the RWGS, which consisted of CO (21), $H_2O$ (26b), unreacted $CO_2$, and also unreacted $H_2$ (29a), as well as by-products (32), mainly small amounts of methane, was withdrawn and supplied to a water separation (7), affording 7.3 t/h of water. This water (26b) was returned to the water electrolysis (5). A total of 2.43 t/h of hydrogen was taken from the water electrolysis, which meant that an additional 14.56 t/h of water was added. The remaining gas mixture (39a) from the RWGS was supplied to a $CO_2$ separation (8). The $CO_2$ separation was effected by amine scrubbing, wherein the separated $CO_2$ (31b) was recycled to the RWGS. The energy for the $CO_2$ separation from the $CO_2$-amine complex formed was obtained from the separation of water (7) from the RWGS gases (39). The gas freed of $CO_2$ (39b) was supplied to the $H_2$/CO separation (9). For the $H_2$/CO separation, a so-called cold box was employed, in which the $H_2$/CO gas mixture was cooled and hydrogen and CO were separated. The separated hydrogen (29c) was returned to the RWGS (6). 11.35 t/h of CO from the $H_2$/CO separation (9) was supplied to a phosgene synthesis (1). Here the CO reacted with 29.79 t/h of chlorine taken from an HCl diaphragm electrolysis (17). 40.15 t/h of phosgene was taken from the phosgene synthesis (1) and reacted in an isocyanate production step (2) with 24.73 t/h of toluenediamine 23 to give 35.27 t/h of toluene diisocyanate (24). This gave rise to 29.59 t/h of HCl gas (25) which, after purification by low-temperature distillation, absorption in water to form 35% hydrochloric acid, and purification of the hydrochloric acid using activated carbon, was supplied to an HCl diaphragm electrolysis (17). Chlorine and hydrogen were taken from the HCl diaphragm electrolysis. The hydrogen was purified and supplied to the RWGS. The toluene diisocyanate (24) obtained was reacted in a conventional manner with polyether polyols (35a) or polyester polyols (35b) to form polyurethane material (37).

After use of the polyurethane material in various commercial applications (80), it can be collected and recycled (90) in order to burn (10b) the polyurethane material waste (38) resulting therefrom. Burning was here realized with oxygen (27) from the water electrolysis (5), resulting in the formation of a highly concentrated $CO_2$ offgas stream (31). This $CO_2$ stream (31) was supplied to a $CO_2$ purification (4) in which water originating from combustion and nitrogen oxides and sulfur oxides were removed. 17.84 t/h $CO_2$ was thereafter supplied to the RWGS (6).

The hydrogen (29) was generated in a water electrolysis with a power of 45 MW in which renewable energy was used. The water electrolysis (5) was an alkaline water electrolysis operated with a current density of 8 kA/m² and a cell voltage of 2 V per electrolysis element. Supplied to this were 45 MW and 21.86 t/h of water plus 7.3 t/h of water from $H_2O$ separation (7). 3.24 t/h of $H_2$ was taken from the water electrolysis.

The RWGS was operated at 802° C., the temperature was generated by burning bio-natural gas.

Through the process of the invention, 22% of the carbon present in the TDI was replaced from a non-fossil carbon source. The use of renewable energy in the water electrolysis allowed the $CO_2$ footprint of the phosgene produced from CO and $Cl_2$ to be further reduced.

The invention claimed is:

1. A process for producing isocyanates and optionally polyurethanes by at least the following steps:
    synthesizing phosgene from carbon monoxide and chlorine,
    reacting phosgene with diamines to form diisocyanates and hydrogen chloride,
    providing a $CO_2$ gas stream,
    purifying the $CO_2$ gas stream of secondary constituents to obtain a purified carbon dioxide,
    electrolyzing water to hydrogen and oxygen,
    providing the hydrogen stream and feeding together with the purified $CO_2$ gas stream as reactants into a reverse water-gas shift reaction (RWGS) reaction zone and reacting the reactants according to a principle of the RWGS reaction to form a product gas mixture consisting of water vapor, CO, and any by-products,
    separating off the water of the water vapor from the product gas mixture and recycling the water to the water electrolysis,
    separating off unreacted carbon dioxide from the gas mixture of the RWGS reaction obtained from the separation and recycling the unreacted carbon dioxide to the RWGS reaction,
    separating off the hydrogen that has not reacted in the RWGS reaction from the gas mixture of carbon monoxide and hydrogen obtained after the separation,
    feeding the remaining carbon monoxide from the separation into the phosgene synthesis,
    feeding the hydrogen from the water electrolysis into the hydrogenation of nitro compounds for the production of diamines,
    separating off and purifying the hydrogen chloride formed in isocyanate production and subsequent oxidative reaction of the hydrogen chloride in the form of a reaction in a thermocatalytic gas-phase oxidation with oxygen to chlorine and water and/or in the form of an electrochemical oxidation of the hydrogen chloride to chlorine and/or in the form of an electrochemical oxidation of the hydrogen chloride to chlorine and hydrogen by HCl diaphragm electrolysis,
    supplying the previously formed chlorine to the phosgene synthesis.

2. The process as claimed in claim 1, wherein the process is a process for producing isocyanates and polyurethanes comprising:
    synthesizing phosgene from carbon monoxide and chlorine,
    reacting phosgene with diamines to form diisocyanates and hydrogen chloride,
    reacting the diisocyanates with polyether polyol and/or polyester polyol to form polyurethanes,
    providing a $CO_2$ gas stream,
    purifying the $CO_2$ gas stream of secondary constituents to obtain a purified carbon dioxide,
    electrolyzing water to hydrogen and oxygen,
    providing the hydrogen stream and feeding together with the purified $CO_2$ gas stream as reactants into an RWGS reaction zone and reacting the reactants according to the principle of the RWGS reaction to form a product gas mixture consisting of water vapor, CO, and any by-products, separating off the water of the water vapor from the product gas mixture and recycling the water to the water electrolysis, separating off unreacted carbon dioxide from the gas mixture of the RWGS reaction obtained from the separation and recycling the unreacted carbon dioxide to the RWGS reaction, separating off the hydrogen that has not reacted in the RWGS reaction from the gas mixture of carbon monoxide and hydrogen obtained after the separation, and feeding the remaining carbon monoxide from the separation into the phosgene synthesis, feeding the hydrogen from the water electrolysis, optionally together with unreacted hydrogen from the RWGS reaction, into the hydrogenation of nitro compounds for the production of diamines, separating off and purifying the hydrogen chloride formed in isocyanate production and subsequent oxidative reaction of the hydrogen chloride in the form of a reaction in a thermocatalytic gas-phase oxidation with oxygen to chlorine and water and/or in the form of an electrochemical oxidation of the hydrogen chloride to chlorine and/or in the form of an electrochemical oxidation of the hydrogen chloride to chlorine and hydrogen by HCl diaphragm electrolysis, supplying the previously formed chlorine to the phosgene synthesis.

3. The process as claimed in claim 1, wherein carbon dioxide provided from a utilization of polyurethane material waste by burning and/or by pyrolysis is used as reactant for the RWGS reaction.

4. The process as claimed in claim 3, wherein the burning is carried out using gas having a content of oxygen gas ($O_2$) of 30% by volume.

5. The process as claimed in claim 4, wherein the gas has a content of oxygen gas ($O_2$) of at least 50% by volume.

6. The process as claimed in claim 1, wherein the water electrolysis and/or the electrochemical oxidation is performed using electricity generated from renewable energy.

7. The process as claimed in claim 1, wherein the water electrolysis and/or the electrochemical oxidation are performed using electricity from feedback energy obtained from burning polyurethane material waste and/or from performing the RWGS reaction.

8. The process as claimed in claim 1, wherein the RWGS reaction is performed using electricity generated from renewable energy.

9. The process as claimed in claim 1, wherein the RWGS reaction is heated by means of feedback energy obtained from burning polyurethane material waste.

10. The process as claimed in claim 1, wherein the process additionally comprises reacting the diisocyanates with polyether polyol and/or polyester polyol to form polyurethanes.

11. The process as claimed in claim 1, wherein the RWGS reaction is heated by burning hydrocarbons from renewable sources.

12. The process as claimed in claim 2, wherein the polyurethanes are, after having been used, recycled as polyurethane material waste and the polyurethane material waste is burned to form carbon dioxide and the carbon dioxide used as feed material in the purification step.

* * * * *